United States Patent [19]

Masuda et al.

[11] Patent Number: 4,685,139

[45] Date of Patent: Aug. 4, 1987

[54] INSPECTING DEVICE FOR PRINT

[75] Inventors: Toshiro Masuda, Tokyo; Kouichi Ishizuka, Koshigaya; Toshiji Fujita, Niiza; Yoshio Kinoshita, Mihara, all of Japan

[73] Assignees: Toppan Printing Co., Ltd.; Mitsubishi Jukogyo Kabushiki Kaisha, both of Japan

[21] Appl. No.: 712,151

[22] Filed: Mar. 15, 1985

[51] Int. Cl.⁴ .............................................. G06H 9/00
[52] U.S. Cl. ...................................... 382/1; 250/562; 250/572; 356/430; 382/34
[58] Field of Search .................... 382/1, 34, 36, 54; 358/106; 356/73, 445, 430, 448; 250/559, 562, 571, 572; 364/551, 552

[56] References Cited

U.S. PATENT DOCUMENTS

| | | | |
|---|---|---|---|
| 3,883,737 | 5/1975 | Throssell et al. | 382/41 |
| 4,349,880 | 9/1982 | Southgate et al. | 382/8 |
| 4,376,951 | 3/1983 | Miyazawa | 356/430 |
| 4,488,808 | 12/1984 | Kato | 356/73 |
| 4,561,103 | 12/1985 | Horiguchi et al. | 382/1 |
| 4,567,506 | 1/1986 | Shinoda et al. | 358/106 |

FOREIGN PATENT DOCUMENTS 2044925A 10/1980 United Kingdom .
2066949A 7/1981 United Kingdom .
2115145A 9/1983 United Kingdom .
2119928A 11/1983 United Kingdom .

OTHER PUBLICATIONS

*Printing Quality Monitoring System for Offset Presses,* (Mitsubishi Heavy Industries, Ltd.), undated brochure.

*Primary Examiner*—Leo H. Boudreau
*Assistant Examiner*—Joseph Mancuso
*Attorney, Agent, or Firm*—Bacon & Thomas

[57] ABSTRACT

The present invention relates to an inspecting device for a print which can scan the entire print pattern of a printed sheet by an optical detecting device, detects the image information of the print pattern at every pixel, calculates the difference between the detected image information with reference information, delays the differential signal in several pixels in the scanning direction of the optical detecting device, calculates the difference between the differential signal and the delayed differential signal, sets a threshold level to the twice differential signal produced from the result, and judges the production of a printing defect when the twice differential signal exceeds the threshold level, thereby accurately detecting the printing defect even when the entire variation in the color density occurs on the printed sheet.

8 Claims, 25 Drawing Figures

F I G. 7
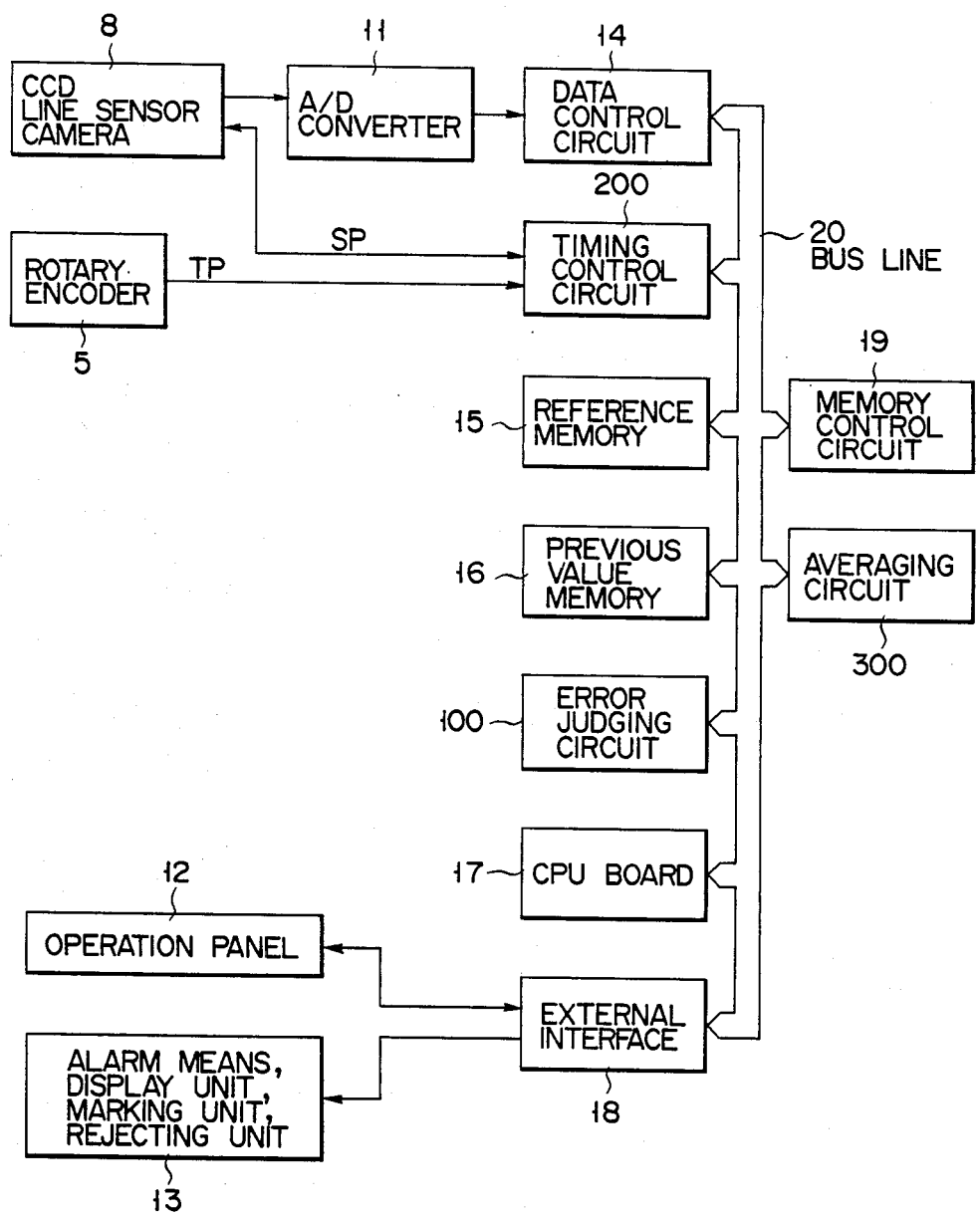

F I G. 16
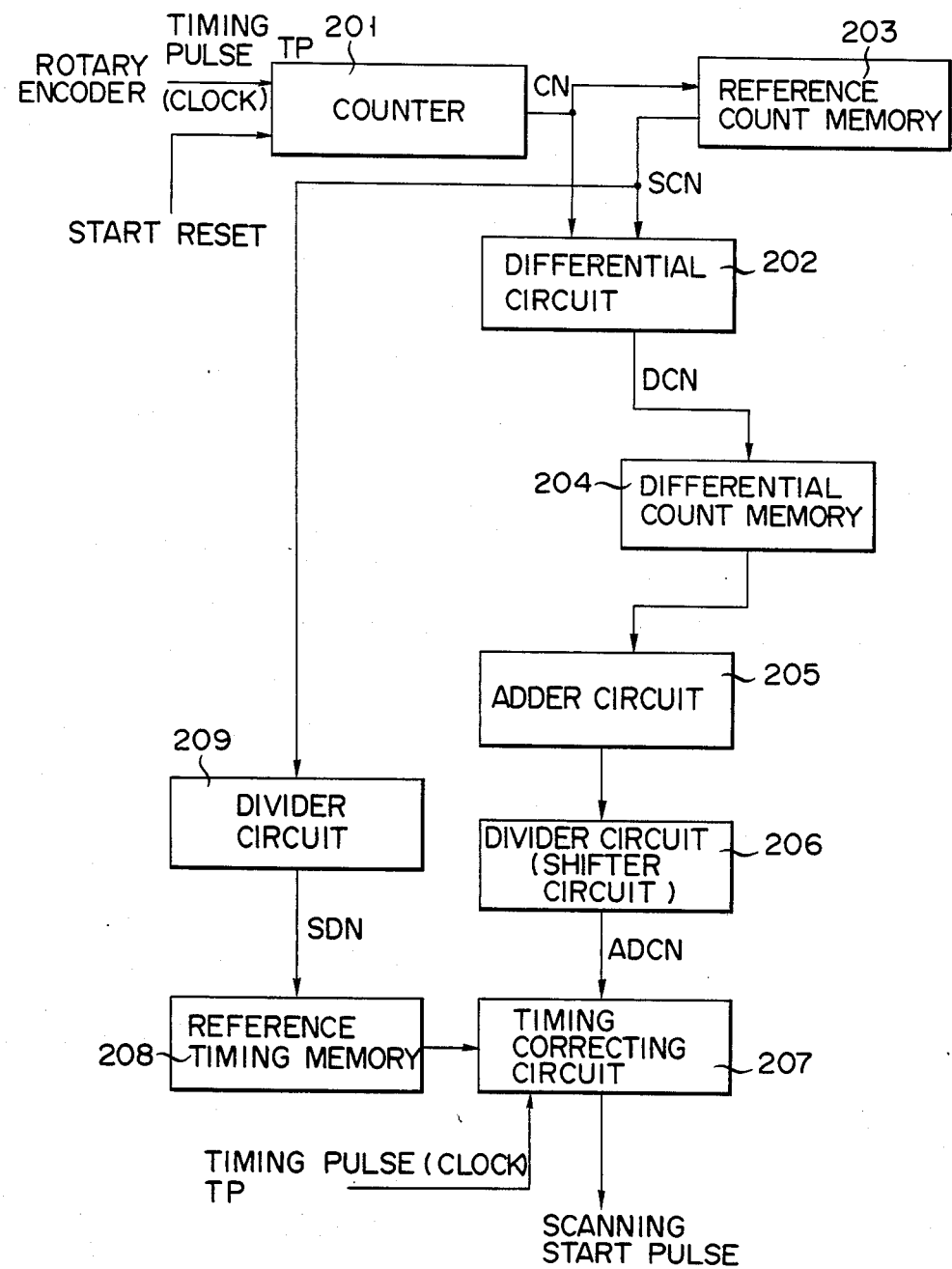

F I G. 19
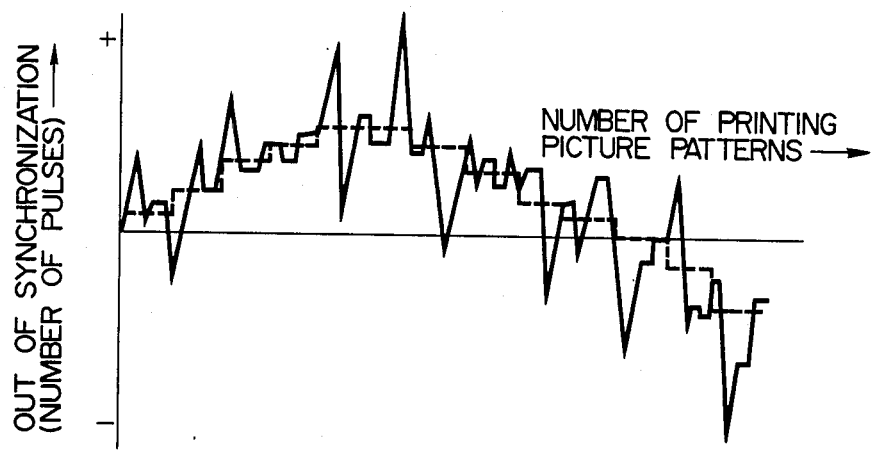
F I G. 20
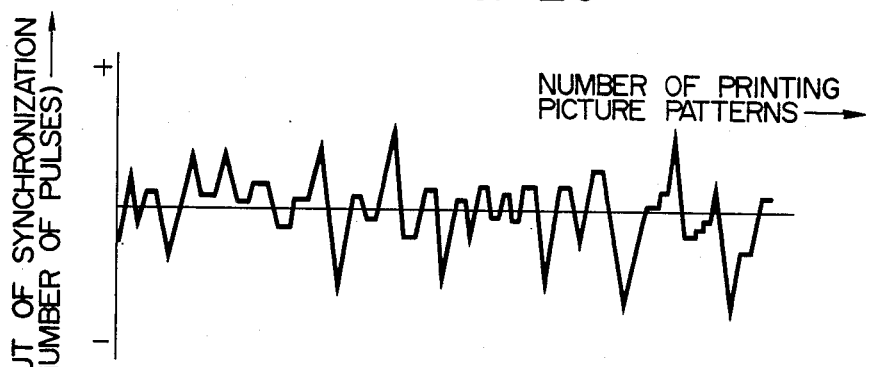
F I G. 21
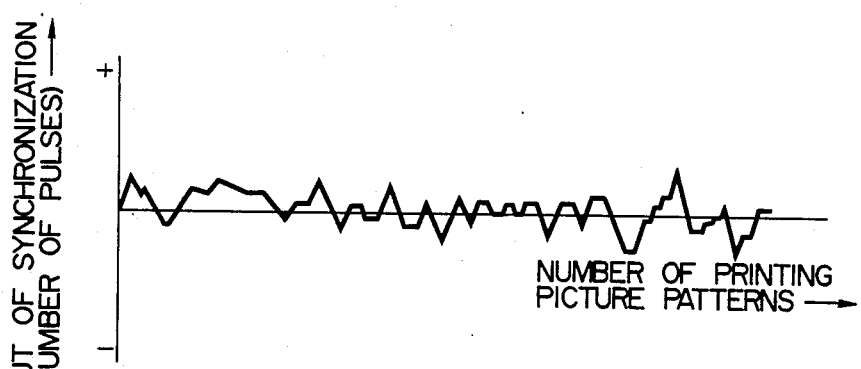

FIG. 22

| NUMBER OF PICTURE PATTERNS | OUT OF SYNCHRO- NIZATION (PULSES) | AFTER CORRECTION | REMARKS |
|---|---|---|---|
| 1 | − 5 | − | NON-INSPECTION MODE |
| 2 | − 3 | − | |
| 3 | − 4 | − | |
| 4 | − 5 | − | |
| 5 | − 7 | − | |
| 6 | − 6 | 0 | REFERENCE SIGNAL INPUTTING MODE |
| 7 | − 7 | 0 | |
| 8 | −10 | 0 | |
| 9 | − 6 | 0 | |
| 10 | − 8 | 0 | |
| 11 | − 5 | − 1 | INSPECTION MODE |
| 12 | − 9 | − 1 | |
| 13 | − 3 | 0 | |
| 14 | − 9 | 0 | |
| 15 | − 6 | 0 | |
| 16 | − 5 | 0 | |
| 17 | − 1 | + 1 | |
| 18 | − 8 | + 1 | |
| 19 | − 4 | + 2 | |
| 20 | − 3 | + 2 | |
| 21 | − 5 | 0 | |
| 22 | − 4 | 0 | |
| 23 | − 5 | 0 | |
| 24 | − 4 | 0 | |
| 25 | − 2 | 0 | |
| 26 | − 8 | 0 | |

INSPECTING DEVICE FOR PRINT

BACKGROUND OF THE INVENTION

I. Field of the Invention

The present invention relates to an inspecting device for print for detecting a defect occurred on the printed sheet by comparing the state of the printed sheet during printing with a reference state in a printing machine.

II. Description of the Prior Art

Heretofore, printed sheets have been inspected one by one by human checker in an off-line. This is because even printed sheets of the same pattern are slightly different due to replenishing ink, changes in the ambient temperature, minor troubles in the printing machine, etc. Only the human visual sense can detect such delicate differences.

On the other hand, various methods have been invented to inspect sheet while they are being printed. In one of them, a strobo is used to illuminate the sheets in synchronism with the printing speed. In another method, a mirror is rotated at high speed, thus applying light onto each sheet. Either method provides a stationary image. The apparatuses employed in these methods cannot inspect the printed sheets. The printed sheets need to be inspected by human checkers. Another trial for inspecting color patches which are printed simultaneously with the picture pattern on the sheet instead of inspecting the entire print area of printed sheet have also been proposed. However, according to this method, when a printing defect such as dripped oil, or stains arise on the print pattern of the printed sheet, the defect might be overlooked, and the function of the inspecting device cannot be sufficiently performed.

A system for inspecting the entire print area of a printed sheet in a sheet-fed press, a rotary press and a rewinder, as disclosed in U.S. Pat. No. 4,488,808 entitled "PRINT INSPECTING DEVICE", by utilizing an optical detecting device provided in the press, has recently been proposed. Since the print pattern of the printed sheet can be automatically inspected in line by utilizing this system, the above-mentioned defect is eliminated, and excellent advantage of the system can be expected.

However, this system still has some problems. As one of the large causes, there is a phenomenon that the color density of a printed sheet entirely varies even in the normal operation as the characteristics of a printing machine. In this system for merely comparing the color density of the print with reference information, it is difficult by this system to judge such defects of the printed sheet. The entire variation in the color density is caused by an inking mechanism, the irregularity in the water supply amount by a damping unit and alteration in the ink amount of an ink fountain, and it is very difficult to suppress such variations in the color density within a predetermined value.

Further, a printed web to be inspected is affected by the influence of variations in a tension, feeding velocity and drying temperature, so that the web is fed in a web rotary press to cause a fine speed variation in the feeding direction. Thus, it is very difficult to accurately synchronize a source of inputting by an optical detecting device an image signal in the feeding direction. The difficulty of the accurate synchronization means different pixels to be inspected in the respective picture patterns of the printed web, and an accurate inspection cannot be fundamentally achieved in the system for inspecting a defect by comparing the print with reference information for each pixel.

Moreover, a printed sheet to be inspected is printed with black, cyan, magenta and yellow ink printing in the ordinary color printing. Even when a printing defect occurs only in one of these colors, the inspecting device must have the function of detecting the defect.

In order to solve this problem, a device for separating a signal light from the printed sheet into wavelength bands by utilizing three color separation filters of R (red: wavelengths of 600–700 nm), G (green: wavelengths of 500–600 nm), and B (blue violet: Wavelengths of 400–500 nm), respectively inputting the three wavelength bands into three CCD cameras, inputting the three wavelength bands into a CCD camera by rotating the R, G and B filters to process the R, G and B signals in a time series, or alternatively flashing light sources of R, G and B to provide similar effects has been proposed so far.

However, according to the above-mentioned conventional inspecting device, there are various drawbacks in practical use such that, though a highly inspecting accuracy can be attained, the device requires a large scale memory capacity, increases in size, cost and a complexity of control system.

SUMMARY OF THE INVENTION

It is an object of the present invention to provide an inspecting device for a print which is capable of accurately inspecting a printed sheet even if an entire variation in color density occurs on a print pattern of the printed sheet.

It is another object of the present invention to provide an inspecting device for a print which allows a circuit arrangement for the inspection to be simplified.

It is still another object of the present invention to provide an inspecting device for a print which is capable of accurately detecting the printing defects of yellow, magenta, cyan and black inks in a color print without separating the respective colors.

It is still another object of the invention to provide an inspecting device for a print which permits an accurate inspection by obviating out of synchronization in case of inputting an image signal due to a fine variations in the feeding direction speed of a web printed sheet even when the present invention is applied to a web press.

In order to achieve the above and other objects, there is provided according to the present invention an inspecting device for a print for inspecting a defect occurred on a printed sheet by scanning an optical detecting device in a direction perpendicularly to the feeding direction of the sheet to detect image information of a print pattern of the fed printed sheet at every pixel, and comparing the image information of the detected pixel with reference information of the corresponding pixel, comprising first differential calculating means for subtracting the detected image information by the reference information, second differential calculating means for subtracting the signal by the signal delayed by several pixels in the scanning direction, and comparing means for comparing the differential signal from the second differential calculating means with an allowable value to output a defect signal when the differential signal exceeds the allowable range, thereby accurately detecting even if an entire variation in a color density occurs in a print picture of the printed sheet.

BRIEF DESCRIPTION OF THE DRAWINGS

FIG. 7 is a block diagram showing a processing circuit of an inspecting device for a print of an embodiment according to the present invention;

FIG. 16 is a block diagram of a timing control circuit in the embodiment of the invention;

FIG. 19 to FIG. 21 are explanatory views showing the state of out of synchronization; and FIG. 22 is an explanatory view showing an example of out of synchronization in each print pattern of the printed sheet.

DETAILED DESCRIPTION OF THE PREFERRED EMBODIMENTS

The present invention will now be described in more detail with reference to the accompanying drawings.

Figure 1:
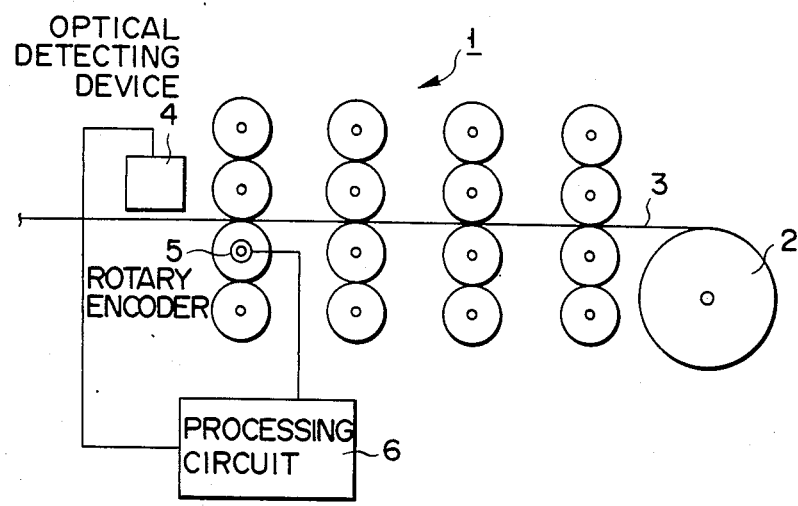
FIG. 1 is a schematic view of an inspecting device for a print of an embodiment according to the present invention.

FIG. 1 is a schematic diagram showing an inspecting device for a print according to the present invention. In FIG. 1, the inspecting device is mounted on a web rotary press, but may be mounted in a sheet-fed press without any problems. In FIG. 1, a web print sheet 3 supplied from a rolled sheet 2 is printed on the front and back surfaces with four colors (black, cyan, magenta and yellow) in a printing unit 1, and then conveyed to a drier and a folding unit (not shown). The inspecting device scan image information of the entire print pattern by a line sensor such as a CCD of an optical detecting device 4 in a direction perpendicular to the sheet feeding direction one by one along scanning lines while taking the timing of sampling by a rotary encoder 5 mounted in the printing unit 1 to input the image information to a processing circuit at each pixel, compares by the processing circuit 6 the image information with reference information, and judges whether the printed state is normal or abnormal, so as to inspect the printed state of the printed sheet. As a result, when the printed state is judged to be defective, the printed sheet causing defect can be recognized to the operator of the press by means such as an alarm, a marking or a rejecting.

The following description will relate to the inspection of one side surface of the printed sheet for readily understanding the present invention, but the other side of the printed sheet may also be inspected entirely in the same manner as the one side surface as will be described.

Figure 2:
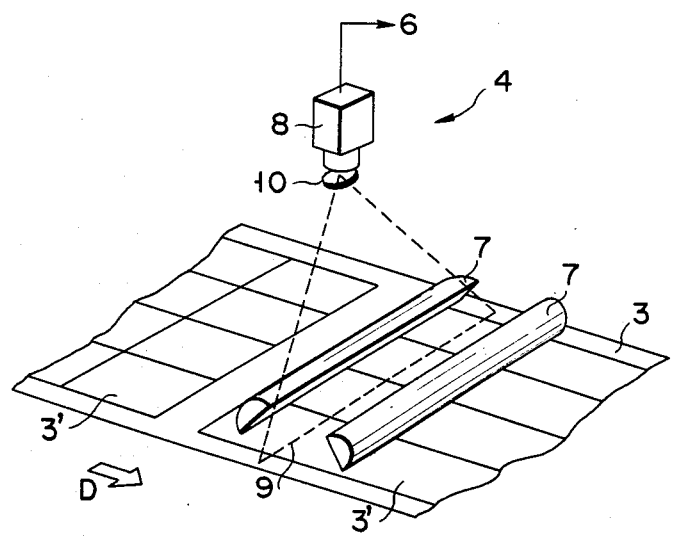
FIG. 2 is an explanatory view of an optical detecting device of FIG. 1.

FIG. 2 shows the construction of the optical detecting device 4. The detecting device 4 has a light source 7 for illuminating the printed sheet, on which prints of the print pattern 3' are sequentially printed on the sheet 3, and a line sensor camera 8 for receiving a light reflected from the printed sheet and photoelectrically converting the reflected light. The light source 7 may use a xenon lamp, a halogen lamp, or a fluorescent lamp which is fired by a DC or a high frequency. The camera 8 may utilize a CCD line sensor or a MOS line sensor. When a close contact line sensor is used, an optical system can be simply adjusted, and the space may be saved. Reference numeral 9 designates a scanning line of the camera 8, which is perpendicular to the feeding direction D of the printed sheet.

Figure 3:
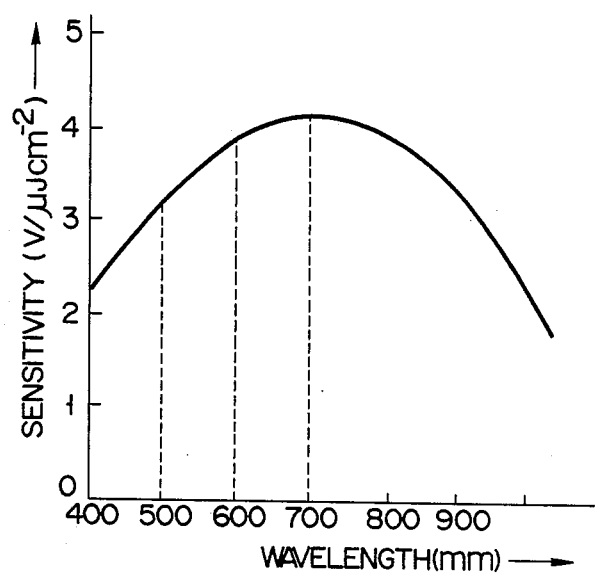
FIG. 3 is a graph showing a spectral sensitivity curve of a CCD line sensor.

When the CCD line sensor is used for the camera 8, an example of the spectral sensitivity curve of the CCD line sensor is understood to have, as shown in FIG. 3, a low sensitivity in the B component of the wavelength band of 400-500 nm and having a peak at 700 nm in such a manner that the curve of the spectral sensitivity ratio of B component:G component:R component is equal to 1:1.3:1.5. FIG. 3 shows the spectral sensitivity curve of the CCD line sensor, and the MOS type line sensor has a similar spectral sensitivity curve to that of the CCD line sensor.

Figure 4:
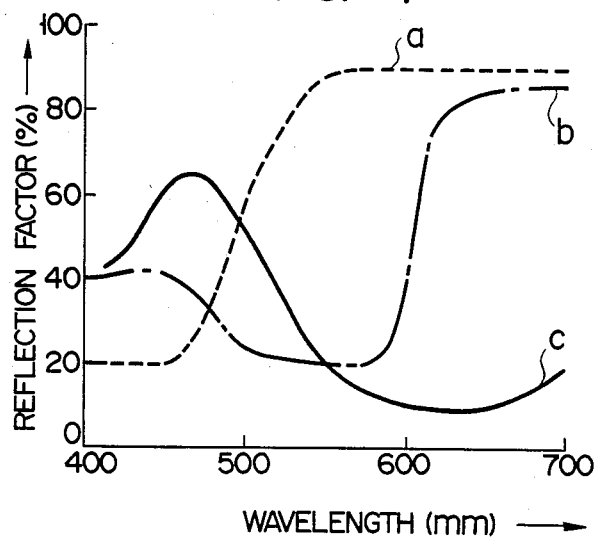
FIG. 4 is a graph showing a reflecting spectral curve of a printing ink.

On the other hand, it is understood that an example of the spectral curves of the reflected lights of printing inks are not completely separated individually to the components of the R, G and B as yellow ink is shown by a broken line a, magenta ink is shown by a dotted broken line b and the cyan ink is shown by a solid line c in FIG. 4, and the influences are effected to the other inks to each other.

Assume that the spectral curve of the light source for illuminating the printed sheet is uniform in 400 to 700 nm and the reflection factor of white sheet is uniformly 90% in 400 to 700 nm, and the reflection factor of the printed portion of 100% dots with the respective inks printed on such a white sheet is obtained on the basis of FIG. 4, and the result is as listed in Table 1.

TABLE 1

|  | 400–500 nm (B content) | 500–600 nm (G content) | 600–700 nm (R content) |
| --- | --- | --- | --- |
| White portion | 90 | 90 | 90 |
| Yellow ink | 25 | 83 | 90 |
| Magenta ink | 37 | 21 | 80 |
| Cyan ink | 56 | 26 | 16 |

(Unit: %)

Therefore, the spectral sensitivity ratio of the CCD line sensors of the B, G and R components is equal to 1:1.3:1.5 as described above, and when the output ratio of the white portion of the printed sheet of the CCD line sensor to the printed portion of 100% dots of the respective inks is obtained from this ratio and the ratio of the white portion of the printed sheet to the B, G and R components of the printed portion of 100% dots of the inks as listed in Table 1 in case that the white portion is 1, the ratio becomes as below.

White portion:yellow ink:magenta ink:cyan ink = 1:0.78:0.54:0.33

As understood from this result, the yellow ink has only 0.22 of the output difference from the white portion of the printed sheet even on the printed portion of 100% dots. Thus, the printing defect of the yellow ink must be detected in the state that range of output level is much lower than those of other inks. For example, when similar variations in the respective color densities arise in the color densities of the yellow ink, and the cyan inks, the output of the CCD line sensor by the variation in the yellow ink is ½ or lower of that by the variation in the cyan ink in response to the above-mentioned output ratio. As apparent from this example, when the light reflected from the printed sheet is in general inputted directly to the line sensor without color separation to inspect the print of the printed sheet, a difficulty results in the detection of the printing defect of the yellow ink as compared with those of the other inks.

The above-mentioned phenomenon occurs in a slight difference between the outputs from the line sensors depending upon the types of the line sensors, the color temperatures of light sources, and the hues of the inks, but the fundamental characteristics are generally similar, with the result that the printing defect of the yellow ink is still difficult in the detection.

Therefore, it is necessary to equalize the outputs of the line sensors for detecting the yellow, magenta and cyan inks in balance so as to accurately detect the printing defects occurred on the prints of the respective inks without color separation. As shown in FIG. 2, according to the present invention, an optical filter 10 which has a spectral transmission characteristic having a peak in the transmission factor in the wavelength band of 400 to 500 nm is disposed as means for equalizing the outputs of the line sensors for the respectively color inks between the line sensor camera 8 and the printed sheet.

When such an optical filter 10 is thus disposed, the light reflected from the printed sheet, which is illuminated by the light source 7, is incident through the filter 10 to the camera 8 to sufficiently provide a different output of the yellow ink to the white portion of the printed sheet, thereby enhancing the detecting accuracy of the yellow ink as compared with the other inks in the same degree as the other inks.

The optical filter 10 will be described in more detail.

Figure 5:
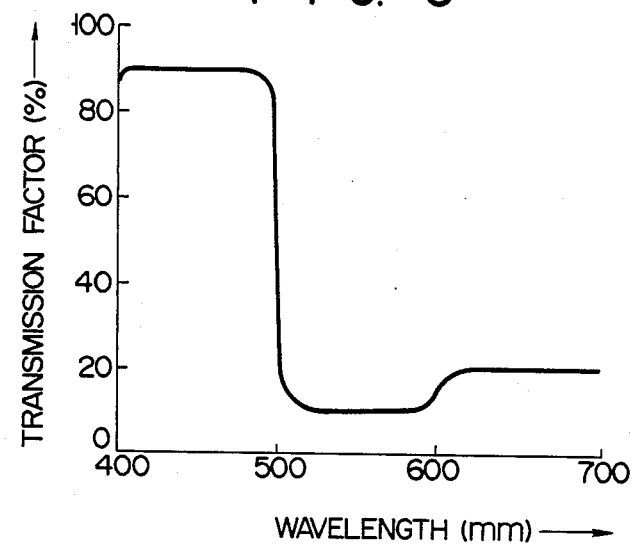
FIG. 5 and FIG. 6 are graphs respectively showing a spectral transmission curve of an optical filter in the embodiment of the present invention.

FIG. 5 shows the spectral transmission characteristic of the optical filter 10 of a model according to the present invention. The filter 10 has, as the spectral transmission characteristics, a 90% transmission factor of the B component (wavelength: 400–500 nm), a 10% transmission factor of the G component (wavelength: 500–600 nm), and a 20% transmission factor of the R component (wavelength: 600–700 nm).

In this example, the transmission factor of the B component is 9 times as that of the G component, and 4.5 times as that of the R component, i.e., the ratio of the spectral transmission factors is 9:1:2 as concrete values. The reason why such a ratio is provided will be described. It is noted that a peak exists in the transmission factor of the B component, and other components (R, G) have larger transmission factor than the color separation filter (B) which is used generally.

The mean transmission factors of the optical filter in the wavelengths of 400 to 500 nm, 500 to 600 nm and 600 to 700 nm are respectively represented by $x_1$, $x_2$ and $x_3$.

The output of the CCD line sensor for the yellow ink can be obtained by the following formula from the spectral sensitivity ratio of the CCD line sensor and the spectral reflection characteristics of the yellow ink as described above:

$$(0.25 \times 1)x_1 + (0.83 \times 1.3)x_2 + (0.9 \times 1.5)x_3$$

Similarly, the outputs of the line sensor for the magenta and cyan inks can be obtained by the following formulae:

$$(0.37 \times 1)x_1 + (0.21 \times 1.3)x_2 + (0.8 \times 1.5)x_3$$

$$(0.56 \times 1)x_1 + (0.26 \times 1.3)x_2 + (0.16 \times 1.5)x_3$$

In order to equalize the outputs of the sensor for the respective color inks, the following equations can be obtained.

$$0.25x_1 + 1.08x_2 + 1.35x_3 = A$$

$$0.37x_1 + 0.27x_2 + 1.20x_3 = A$$

$$0.56x_1 + 0.34x_2 + 0.24x_3 = A$$

When these equations are solved, $x_1:x_2:x_3 = 9:1:2$ is obtained. Therefore, 9:1:2 of the optimum spectral transmission factor ratio of the respective B, G and R components can be attained.

Since this calculation is based on the integration similarly to a straight line, it is desired to obtain the more accurate transmission factor ratio at every 10 nm by the integration by utilizing a computer.

Therefore, the optical filter which has the spectral transmission factor as shown in FIG. 5 can be provided by designing the actual optical filter on the basis of the spectral transmission factor ratio of 9:1:2 to be incorporated.

By using such an optical filter, the output ratio of the CCD line sensors becomes as below.

White portion:yellow ink:magenta ink:cyan ink = 1:0.5:0.5:0.5

Thus, the outputs of the line sensors for the respective color inks can be equalized in balance, and the output ratio of sufficiently high difference between the white portion of the printed sheet and the other color inks can be provided. Consequently, similarly high detecting accuracy can be provided in the line sensors for the respective color inks.

This example depends upon the spectral sensitivity curve of the CCD line sensor shown in FIG. 3 and the spectral reflection curve of the ink shown in FIG. 4. However, other line sensors or other types of inks are substantially similar in the curves as shown in FIG. 3 and/or FIG. 4, and the difficulty in the detection of the printing defect of the yellow ink is still similar so that the optical filter as described above is advantage of detecting the printing defects in yellow ink.

Therefore, when the optical filter has a peak in the transmission factor of 400 to 500 nm of the wavelength band and the spectral transmission curve having the transmission factor of the degree capable of obtaining the necessary output for detecting the printing defect in other visible light wavelength bands, the difficulty in the detection of the printing defect of the yellow ink can be eliminated.

As the actual optical filter, it has been confirmed that when the filter had the transmission factor of the B component of approximately twice as that of the other component, the output ratio of the line sensor could be remarkably improved through this optical filter and the difficulty in the detection of the printing defect of the yellow ink could be obviated.

When the optical filters sold in the market at present are selected depending upon the subject matter of the present invention as described above, No. 38 or No. 79 of the optical filter manufactured by Eastman Kodak Company can be applied.

Figure 6:
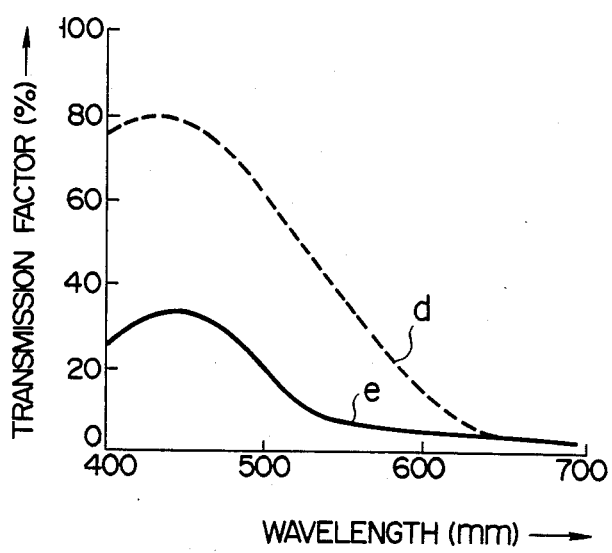

FIG. 6 shows the spectral curve d of the No. 38 and the spectral curve e of No. 79. Both curves have peaks in the transmission factor of the B component and the transmission factors of the B components of these filters are twice or more as those of the G and R components, and the transmission factor of G and K components are sufficient of detecting the other color ink. The fact that when the optical filter described above is used as the optical filter 10 shown in FIG. 2, the difficulty in the detection of the printing defect of the yellow ink can be eliminated, can be experimentally recognized.

It is preferable to use an infrared cut-off filter since the line sensor causes an oozing phenomenon in an infrared ray (wavelength: 700 nm or higher).

Table 2 shows the outputs of a CCD line sensor measured in case that only the infrared cut-off filter and the combination of No. 38 of the optical filter and the infrared cut-off filter are mounted between the CCD line sensor and the respective color inks are printed in 100% dots. The quantity of light is reduced by the use of the filter of No. 38, but the gain is adjusted by an amplifier, and the output level of the line sensor from the white portion of the printed sheet are equalized between only infrared cut-off filter and combination of No. 38 and infrared cut-off filter.

TABLE 2

|  | Only infrared cut-off filter | | Infrared cut-off filter + No. 38 | |
| --- | --- | --- | --- | --- |
|  | Output | Difference from white | Output | Difference from white |
| White portion | 2.2 | — | 2.2 | — |
| Yellow 100% | 2.0 | 0.2 | 1.7 | 0.5 |
| Magenta 100% | 1.6 | 0.6 | 1.2 | 1.0 |
| Cyan 100% | 0.6 | 1.6 | 1.0 | 1.2 |
| Black 100% | 0.1 | 2.1 | 0.1 | 2.1 |

(Unit: V)

From the above-mentioned result, the output difference of the line sensor between the yellow ink and the white portion of the printed sheet becomes 2.5 times by employing the filter of No. 38, and the detecting accuracy of the line sensor with the above-mentioned optical filter can be remarkably improved as compared with the conventional line sensor with only the infrared cut-off filter.

The output difference of the line sensor between the magenta ink and the white portion of the printed sheet becomes approximately 1.7 times, and a similar advantage can be provided. The output difference of the line sensor between the cyan ink and the white portion of the printed sheet becomes 0.75 times, which is still higher than the magenta ink and causes no problem in the detection.

As described above, it has been also confirmed experimentally that the output ratio of the respective inks from the CCD line sensor could be improved by employing the No. 38 of one type of the optical filter having the above-mentioned characteristic according to the present invention.

The image information of the print pattern inputted by the optical detecting device 4 as described above is fed to the processing circuit 6, which inspects the presence of the defect occurred on the printed sheet 3.

FIG. 7 shows a block diagram of the processing circuit 6. The rotary encoder 5 mounted in the printing machine is connected to a timing control circuit 200, which calculates a scan-starting pulse SP of the CCD line sensor camera 8 on the basis of a timing pulse TP from the encoder 5, and transforms the pulse SP to the camera 8. In a sheet-fed press, the pulse SP may directly utilize the pulse TP generated from the encoder 5, because out of synchronization caused by the infinitesimal variation in the feeding direction speed of the printed sheet does not occur in the sheet-fed press.

The camera 8 is connected to an A/D converter 11, and transfers the image information of the print pattern of the printed sheet as analog information in a direction perpendicular to the feeding direction of the printed sheet at every pixel to the converter 11 on the basis of the pulse SP. The converter 11 is connected to a data control circuit 14, converts the analog image information transferred from the camera 8 into a digital signal at every pixel, and transfers the digital signal into the control circuit 14.

The data control circuit 14 receives and delivers the digital image information to a bus line 20 as inspecting information, and has functions of accelerating the data transfer, controlling the timing of receiving and delivering the data, and buffering the data.

A reference memory 15 is connected to the bus line 20 and stores reference information at every pixel as the reference of the inspection. When an operator of the printing machine visually observes the print pattern of the printed sheet and judges that the printed sheet during printing at present is normal and has sufficient printing quality as the reference of the inspection, the operator instructs inputting of the reference information on an operation panel 12, and the print pattern information inputted from the camera 8 is resultantly stored in the memory 15 through the converter 11 and the control circuit 14 described above.

The memory 15 and a previous value memory 16 (to be described in detail later) are controlled by a memory control circuit 19 for storing the data and reading out the data.

The operation panel 12 is connected to an external interface 18 to instruct the entire inspecting device. The instruction signal is transferred through the interface 18 to a CPU board 17, which controls the circuits in accordance with a program stored therein.

When the reference information is stored in the memory 15, the processing circuit 6 is shifted to an inspection mode. In the inspection mode, the image information of the print pattern of the printed sheet which is sequentially printed is delivered from the camera 8 through the converter 11 and the control circuit 14 to an error-judging circuit 10 as the information to be inspected.

In this case, the reference information in the same address as the information to be inspected is simultaneously delivered from the memory 15 to the judging circuit 100, which compares and calculates the information to be inspected with the reference information to inspect the error or defect occurred on the print pattern of the printed sheet. When the judging circuit judges the presence of the defect, an error signal is transferred to the CPU board 17, which thus operates alarm means such as a display unit, a marking unit or a rejecting unit through the interface 18, thereby notifying the operator of the printing machine for the presence of the defect.

When the judging circuit 100 judges the defect, it is required to accurately inspect the defect by eliminating the influence of the variation in the color density of the entire printed sheet as described above.

Figure 9:
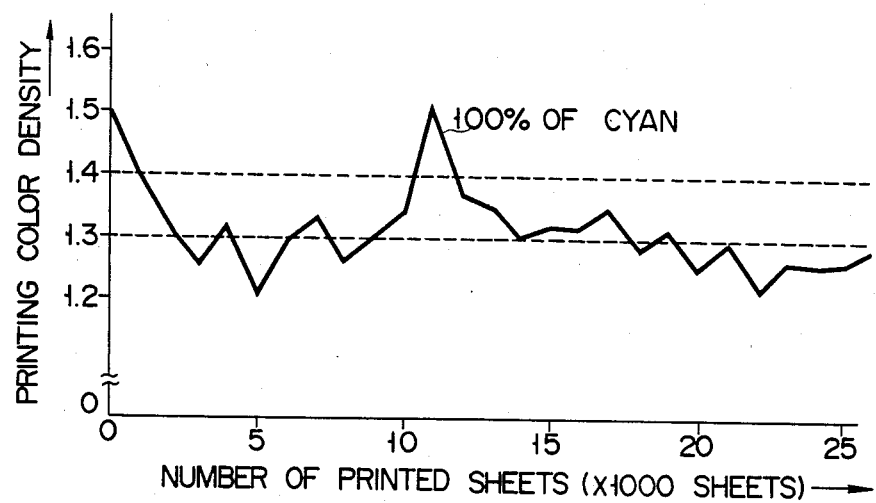
FIG. 9 is an explanatory view of a case that an entire variation in a color density occurs on a printed sheet.

FIG. 9 shows an example of the case that variations in the color density occurs on the print pattern of the entire printed sheet.

FIG. 9 is a graph illustrating the measured reflection density (through R filter) of 100% dots of cyan of the printed sheet at every 1000 sheets after print starting. The reference color density of 100% dots of cyan is 1.3 to 1.4 as designated by a broken line, while it is understood from FIG. 9 that the actual variation in the color density of the printed sheet as designated by a solid line is very large. As described above, the causes of the variation in the color density include the quantity of inks in ink fountains, the periodicity of supplying inks through an ink roller arrangement, balance with dampening water, the content of the print pattern, etc. It is said to be very difficult at present to suppress the variation in the color density by obviating the respective causes one by one. Therefore, it is said to be difficult to sufficiently improve in practice the inspecting accuracy in a system for comparing the image information with the reference value due to the quantity of the present reflecting light unless the printed sheet is inspected by eliminating the influence of the variations in the color density of the entire printed sheet.

Figure 10A:
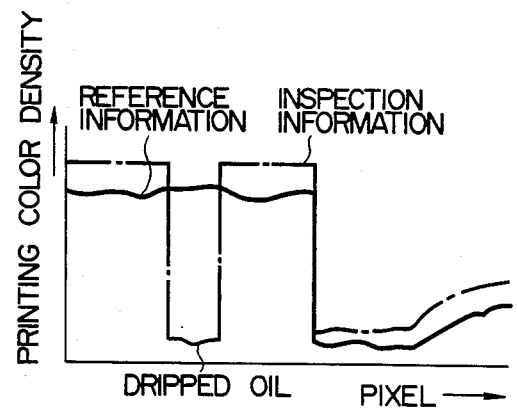
FIG. 10a, FIG. 10b, FIG. 11a, FIG. 11b, FIG. 12a, FIG. 12b, FIG. 13, FIG. 14 and FIG. 15 are diagrams of the models of printing defects for describing the operation of the embodiment of the invention.
Figure 10B:
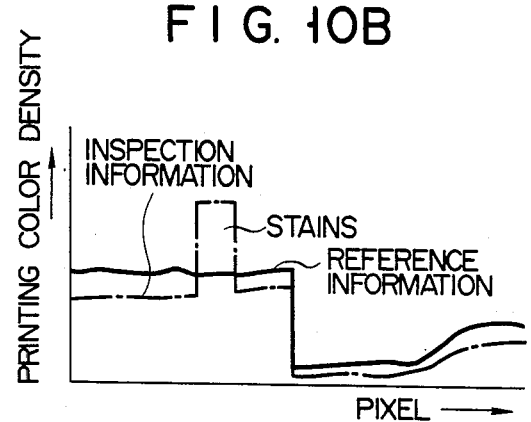

FIGS. 10 show a printing defect in the inspection of a printed sheet in a model. FIG. 10(A) shows the image information at every pixel in case that a printing defect such as dripped water or oil occurs on a printed sheet by a one-dotted chain line and the reference information at the normal time by a solid line. FIG. 10(B) shows the image information at every pixel in case that stains occur as a printing defect on the printed sheet by a one-dotted chain line and the reference information at the normal time by a solid line. In FIG. 10(A), the drop of the density due to dripped water or oil is observed in the state that the color density of the detected image information to the reference information is entirely increased in height by the influence of the variation in the color density of the entire printed sheet. In FIG. 10(B), the rise of the density due to the stains is observed in the state that the detection signal is entirely decreased with respect to the reference information.

Figure 11A:
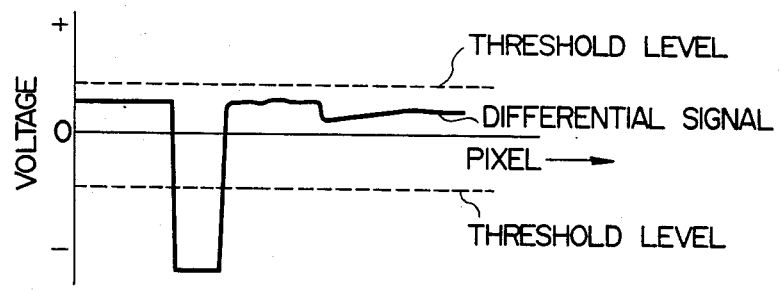
Figure 11B:
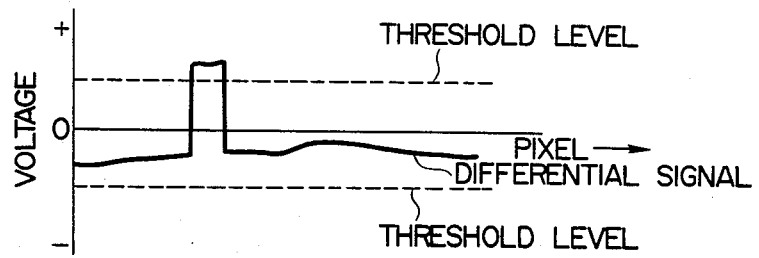

The case applied directly with the comparing and inspecting method in which the difference between the detected image information and the reference information is produced and when the differential value exists in a predetermined range, it is judged as normal as the representative comparing and inspecting method is shown with respect to the model shown in FIG. 10(A) and FIG. 10(B), in FIG. 11(A) and FIG. 11(B), respectively.

In FIG. 11(A) and FIG. 11(B), broken lines are threshold levels, and a solid line is the value of the difference between the detected image information and the reference information. In this case, the printing defect can be inspected by setting upwardly the level of the threshold value, but when the entire variation in the color density increases more, the entire signal exceeds the threshold level to cause an impossibility in judging, or even if the width of the variation in the signal due to the printing defect is absorbed to the width of the entire variation in the color density so that the remarkable printing defect does not cause the signal to exceed the threshold level, thereby possibly disabling to detect the printing defect.

In order to eliminate the entire variation in the color density which affects adverse influence to the judgement of the printing defect before judging, the threshold value is set to the twice differential signal produced by taking the difference between the differential signal (e.g., the signal designated by the solid line in the model in FIG. 11) produced by taking the difference between the detected image information and the reference information and a signal displaced (delayed) by several pixels (3 to 5 pixels) from the differential signal in the scanning direction.

Figure 12A:
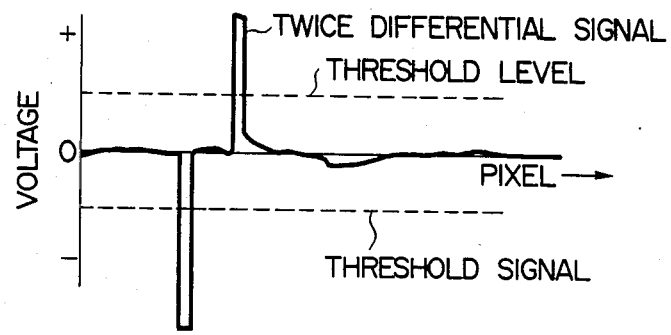
Figure 12B:
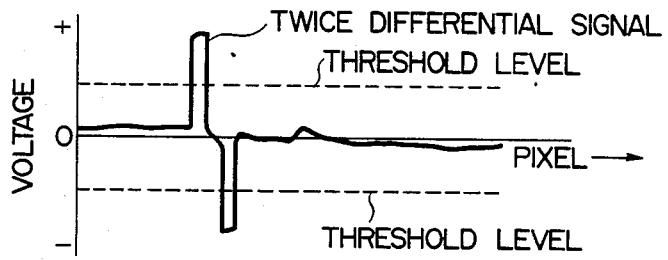

FIGS. 12 show the twice differential signals processed as described above. FIG. 12(A) shows the signal shown in FIG. 11(A) processed as described above, and FIG. 12(B) shows the signal shown in FIG. 11(B) similarly processed as described above. As apparent from FIG. 12, the presence of the printing defect can be judged (i.e., setting the threshold level) in the state that the influence of the entire variation in the color density is eliminated by the above-mentioned process.

The twice differential signal produced by the above-mentioned process results in the similarity apparently to the signal produced by analog differentiating the analog differential signal produced by taking the difference between the detected image information and the reference information, but has the following large advantages as compared with the process by the analog differentiation.

First, according to the above-mentioned process of the present invention, only the differential calculation is sufficient, and the circuit arrangement in the digital circuit is advantageously more simple than that of the analog differentiating calculation.

Figure 13:
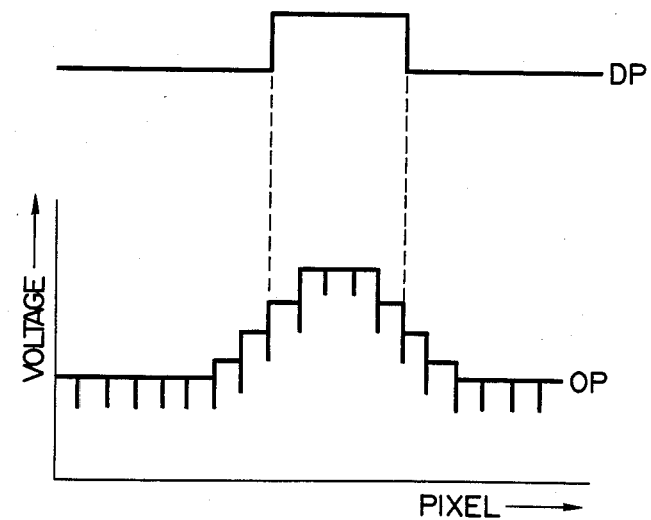
Figure 14:
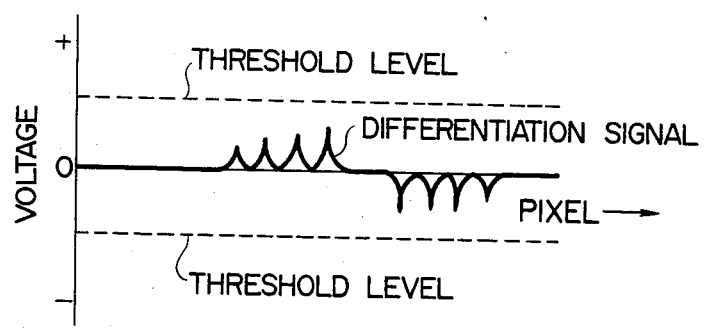

Second, as shown in FIGS. 13, a leakage phenomenon to adjacent pixels occurs in the rise and fall of the color density of the print pattern in the CCD line sensor for inspecting the printing defect with respect to the density pattern DP of the print pattern, and the signal is outputted in the insensitive state as designated by a pattern OP. When this signal is differentiated, a signal difference is not almost presented as shown in FIG. 14 even if the original signal has a considerably signal difference, the varying points are concealed by the influence of the entire variation in the color density described above, and the printing defect cannot be resultantly inspected.

Figure 15:
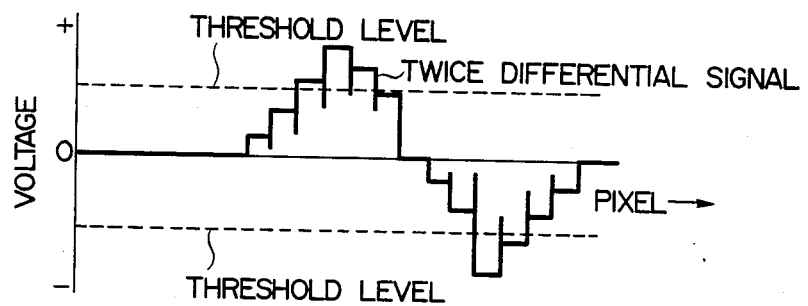

However, according to the method of taking the difference from the differential signal with the signal delayed by four pixels in accordance with the present invention, a large signal difference can be produced at the varying point as shown in FIG. 15, and the threshold level can be accordingly readily set.

When the number of delaying pixels of the signal is set to four according to the present invention as described above, the printing defect occurred slowly in the variation in the color density can also be accurately detected at the color density varying point of the printing defect of the entire variation in the color density of the printed sheet by alleviating the influence of the oozing phenomenon of the CCD line sensor or the MOS line sensor.

In this example, even if the number of delaying pixels of the signal is set to 1 to 2 pixels, the varying point can be detected, but the signal difference cannot be considerably increased, and the effect does not become remarkable. When the number of delaying pixels of the signal is set to 6 or more pixels and the difference is taken, there arises a disadvantage that a peak time width increases and the varying point becomes uncertain. Therefore, the preferable number of delaying pixels is 3 to 5.

Further, even if the entire color density is abnormally increased or decreased, the color tone of the printed sheet is broken, and this printed sheet must be detected as an improper printed sheet. However, when this printed sheet is processed as described above, the printed sheet is inspected in the state that the entire variation in the color density is removed. Accordingly, the defect of the printed sheet of the case that the entire variation in the color density of the printed sheet exceeds the allowable range cannot be detected. In order to supplement this inspection, the differential value of the signal produced by taking the difference between the color density detection information from the print pattern of the printed sheet and the reference information is accumulated in advance in the amount corresponding to a predetermined number of pixels, the reference values of the upper and lower limits to the accumulated value are set, and when the accumulated value exceeds the reference value, it is judged that the entire abnormal variation in the color density occurs.

The printing defect such as dripped water or oil, and stains can be detected and the entire abnormal variation in the color density can also be preferably detected by adding the second process described above to the previous first process.

The error-judging circuit 100 which can process, as described above, has a circuit arrangement shown in FIG. 8, and the error-judging circuit will be described in detail with reference to FIG. 8.

As described above, image information at every pixel to be inspected and reference information from the reference memory 15 are synchronized, and inputted to the error-judging circuit 100. The judging circuit 100 calculates the difference between the image information and the reference information by a first differential circuit 101 and produces a first differential signal DIS. This signal DIS corresponds to the signal designated by the solid line in FIG. 11. The first differential circuit 101 is connected to second differential circuit 102, a delay circuit 103 and an accumulation counter 106.

The delay circuit 103 produces a delay signal DDS delayed by 3 to 5 pixels from the differential signal DIS in the scanning direction, and is connected to the second differential circuit 102.

The second differential circuit 102 calculates the difference between the signal DIS and the delay signal DDS, and produces a twice differential signal SDS. This signal SDS corresponds to the signal designated by the solid line in FIG. 12.

The second differential circuit 102 is connected to an absolutizing circuit 104, and the twice differential signal SDS produced by the differential circuit 102 is absolutized by the circuit 104. The absolutization of the twice differential signal SDS means the inspection is executed by one comparing circuit without providing two upper and lower limit comparing circuits, and when the two comparing circuits are provided, the absolutizing circuit 104 can be eliminated.

The absolutizing circuit 104 is connected to a first comparing circuit 105, which judges whether the absolutized second differential signal is larger than a threshold level signal SH1 or not. The signal SH1 is applied from the CPU board 17, and may be fixed or variable depending upon the magnitude of the reference information.

When the absolutized twice differential signal exceeds the signal SH1 as a result of comparison in the comparing circuit 105, an error signal ER1 is transferred to the CPU board 17.

On the other hand, to judge the error or defect of the case that the entire variation in the color density is excessively large as described above, the signal DIS from the circuit 101 is accumulated in the counter 106 for one print pattern. The counter 106 is connected to the absolutizing circuit 107, which absolutizes an accumulation count signal ICS. The absolutizing circuit 107 is to operate with only one comparing circuit as described above.

The absolutizing circuit 107 is connected to a second comparing circuit 108, which compares the absolutized accumulation count signal with a threshold level signal SH2, and transfers an error signal ER2 to the CPU board 17 when the signal ICS exceeds the signal SH2.

The signal SH2 applied from the CPU board 17 may be fixed or may be arbitrarily set.

The counter 106 is reset when one print pattern of the printed sheet is completely inspected.

According to the error-judging circuit 100 as described above, the circuit 100 can accurately inspect the printed sheet even if the entire variation in the color density occurs on the printed sheet to be inspected by comparing the second differential signal with an allowable value, but in a web rotary press, a delicate speed variation occurs in the feeding direction of a web-printed sheet as described above, and there arises a problem of out of synchronization in case of inputting print pattern information.

Figure 18:
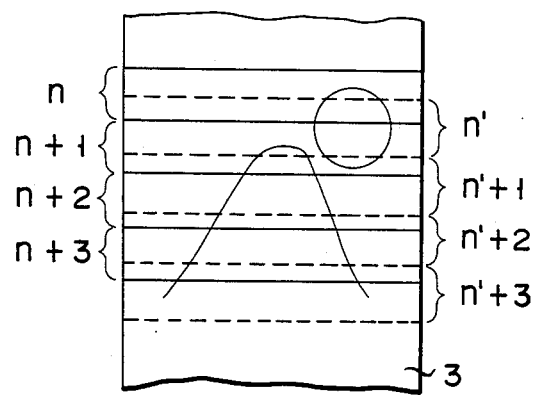
FIG. 18 is an explanatory view showing the state of out of synchronization in the scan timing.

The out-of-synchronization as shown in FIG. 18 means a phenomenon that a scanning line for sampling in according with the timing pulse from the rotary encoder becomes different at every signal inputting time. In other words, print pattern information is inputted along the scanning line of n, n+1, ... in the scanning of a certain print pattern of the printed sheet, but the information becomes print pattern information along the scanning line of n', n'+1, ... in the next scanning of the print pattern of the printed sheet. In this state, it is fundamentally impossible to judge the printing defect by comparing the detected image information and the reference information due to the difference between the pixels.

Since the variation in the printing speed, the variation in the tension, the elastic and plastic deformations of a sheet to be printed, and further the variation in the temperature in a drier of causes for the out-of-synchronization are based on the fundamental mechanism of a printing machine, it is impossible to all ignore them at present, and it is said to be difficult to accurately take the synchronization only by the rotary encoder 5.

FIG. 19 shows a graphical diagram of the measured result (synchronizing characteristic) of the displacement of synchronization of a printing machine at the normal operation time (400 rpm) in a model manner. When the variation in speed is converted to the print pattern, there is an irregularity of approximately several mm of the displacement with respect to the reference length. It is understood that this irregularity results from the combination of the large periodic wave over several hundreds of the number of print patterns and the small periodic wave of the fact that the displacements alternatively become large and small at every other print pattern, and ranges in approximately several mm.

First, in the inspecting device according to the present invention, the influence of the long periodic wave of several hundreds of the number of the print patterns of the variations of the displacement of the synchronization shown in FIG. 19 is eliminated. For that purpose, as shown in FIG. 19, a plurality of print patterns are used as a set (e.g., 5 to 20 print patterns are used as a set), the average value (designated by a broken line) of the displacement of the synchronization is calculated, and then fed back, and the displacement of the synchronization of the one periodic length of one print pattern of next set is corrected. Thus, the influence of the long periodic wave can be substantially eliminated. The use of the average value of the displacements of synchronization of the one periodic length of the print patterns of the unit of predetermined number of sheets for the correction of the displacement of synchronization of next set of the print pattern is not defective because the difference of the average values of the displacements of synchronization of adjacent sets is extremely small since the period of the wave is long like several hundreds of sheets.

This process will be described in more detail by using a model case.

Assume that 1000 timing pulses are generated from the rotary encoder for one print pattern of the printed sheet and 100 scans are carried out for one print pattern, a scan starting signal SP for scanning once per 10 pulses is fed to the CCD line sensor camera 8 in 1000 pulses and 100 scans in the state that the displacement of synchronization is 0. However, the scanning lines are unstable due to the displacement of synchronization as shown in FIG. 22 as they are, and therefore large displacement occurs at every print pattern. Thus, in this model case, the number of the print patterns of the printed sheet to take the average value of the displacements of synchronization is set to 10 sheets, and the average value of the displacement of synchronization per one print pattern is calculated. In example FIG. 22, −6 pulses at first to 10th sheets, and −5 pulses at 11th to 20th sheets. In other words, when the printed sheet is normal, 1000 pulses must be generated for one print pattern. 994 pulses in average at first to 10th sheets, and 995 pulses in average at 11th to 20th sheets. Thus, there arises the displacement of synchronization due to the delicate variation in the speed as described above.

When the necessary number of corrections to correct the displacement of synchronization are −6 pluses, this value is fed back, it becomes 100 scans/6 pulses=17 scans in the set of next print pattern, it is not 10 pulses at every 17 scans (totally 6 times), but a sampling start signal is transferred at 9 pulses. Further, when the necessary number of corrections are −5 pulses, it becomes 100 scans/5 pulses=20 scans, and it is set that the sampling start signal is transferred at an interval of 9 pulses per one scan at every 20 scans (totally 5 times).

When the above-mentioned process is sequentially executed, the displacement of synchronization in the average of 10 print patterns can be eliminated. Accordingly, the displacement of synchronization of long period in the entirety can be obviated.

As described above, the average value of the displacements of synchronization per one print pattern of the printed sheet is calculated with a plurality of print patterns as a set, and the displacement of synchronization of the print patterns of a plurality of sheets of the next set is corrected. Then, the displacement of synchronization presented as a long and large periodic wave as shown in FIG. 20 can be eliminated.

According to the present invention, the influence of the short periodic wave at every several print patterns can be reduced to the ignorable degree.

As shown in FIG. 18, assume that the scanning lines are n, n+1, n+2, . . . for print pattern of the printed sheet in a certain scanning, the scanning line becomes n', n'+1, n'+1, . . . in the scanning for the next print pattern, and the displacement is M mm. The imaginary scanning line is set to the intermediate between both the scanning lines by averaging the image information inputted by the two print patterns of the printed sheet, and the displacement of this case can be accordingly suppressed to M/2 mm.

In the embodiment described above, the number of the print patterns to be averaged to obtain the imaginary scanning line is two. However, the number of the print patterns is not limited to two, but may be three times or more. However, in view of the generating characteristic of the printing defect, the printing defect due to dripped water might, for example, occur only on the print patterns of several (3 to 5) of printed sheets. In this case, when a number of print patterns are averaged, the color density level of the printing defect is absorbed to the density level of the normal print patterns of the most remaining print patterns, and the printing defect cannot be detected. Therefore, the number of print patterns to be averaged is preferably set to several by considering the occurring frequency of the printing defect (dripped oil or water) occurred at random on the print patterns of the printed sheet according to the density level.

FIG. 21 shows the state that the averaging process (two print patterns are averaged) is executed by the above-mentioned method for the synchronizing characteristic of the state that the long periodic displacement of synchronization shown in FIG. 20 is eliminated. As a result, the displacement of synchronization is suppressed to approximately 1/5 of the state shown in FIG. 19, the influence of the displacement of synchronization is not affected, and the improper synchronization can be obviated at this point.

As described above, the improper synchronization can be suppressed to the level which is not defective in practical use, but, in the actual inspection of the printed sheet, the reference signal to be compared with the signal to be inspected is inputted from the normal printed sheet. When the reference signal is inputted in the state of displacement of synchronization, the reference signal itself is not accurate, and the resultant inspection becomes meaningless. In order to eliminate such drawbacks, it is necessary that the reference signal is inputted at the signal when the displacement of synchronization is 0 as the reference signal, or the average of the signals to be inspected of a plurality of sheets (sufficiently large) is inputted as the reference signal. As a result, the inspecting device can compare the signal to be inspected with the reference signal and judge the printing defect in the state that the error in the detected signal due to the displacement of synchronization is minimized.

A circuit arrangement for processing to eliminate the displacement of synchronization as described above will be described in detail.

FIG. 16 is a block diagram showing a timing control circuit arrangement for eliminating the displacement of synchronization of the above-mentioned long period.

In FIG. 16, a timing pulse TP from the rotary encoder 5 is inputted to a counter 201, which counts the number of timing pulses TP for one print pattern of a printed sheet and outputs a count number CN. In this case, the counter 201 may be started and reset by the start of the print pattern, or a starting mark may be simultaneously printed on a printed sheet.

The counter 201 is connected to a reference count memory 203 and a differential circuit 202.

The memory 203 stores the count number CN of the timing pulses of the print pattern of the printed sheet when inputting the above-mentioned reference information. The memory 203 is connected to the differential circuit 202, and used as a reference count number SCN for comparing with the counted number of the print pattern to be inspected of the printed sheet after starting the inspection.

The differential circuit 202 calculates the difference between the count number CN of one print pattern during inspecting and the reference count number SCN, and transfers a differential count number DCN (corresponding to the displacement of synchronization) as the result to a differential count memory 204. The memory 204 stores the differential count number DCN in the amount corresponding to predetermined number of print patterns (10 patterns in the above example). The memory 204 is connected to an adder circuit 205, which calculates the sum of the count number DCN of the predetermined number of the print patterns. The adder 205 is connected to a divider circuit 206, which divides it by the predetermined number of print patterns, thereby producing the average value ADCN of the count number N (corresponding to the amount of displacement of synchronization for one print pattern). In this case, when the predetermined number is $2^n$, it is fast in the calculating speed by using a shifting circuit instead of the divider circuit.

The count number SCN from the memory 203 is, on the other hand, transferred to the divider circuit 209, which divides the count number SCN by a predetermined scanning line number and produces a reference scanning interval pulse number SDN. The divider 209 is connected to a reference timing memory 208, which stores the pulse number SDN. The divider 209 and a reference timing memory 208 are connected to a timing correcting circuit 207, which counts a timing pulse TP for the print patterns of the next set on the basis of the reference scanning interval pulse number and the average value ADCN per one print pattern in one set and generates a scan starting pulse SP. In case that the average value ADCN is 0, the timing pulse TP is counted in the amount corresponding to the pulse number SDN, and a scan-starting pulse SP is generated.

When the average value ADCN is negative, the scan-starting pulse SP is generated at an equal interval in the absolute value of the average value ADCN in one print pattern at an interval smaller by 1 than the pulse number SDN. When the average value ADCN is positive, the scan-starting pulse SP is generated at an equal interval in the absolute value of the average value ADCN in one print pattern at an interval larger by 1 than the pulse number SDN. Since these circuits have a margin in the calculating time for calculating at every one scan, an exclusive microprocessor is used and programmed.

When the timing pulse TP is not sufficiently shorter in the interval than the starting pulse SP, the pulse TP may be replaced with clocks shorter than the starting pulse.

As described above, the CCD line sensor camera 8 can be scanned at the timing for eliminating the displacement of synchronization of a long period as shown in FIG. 20.

Then, a circuit for removing the displacement of synchronization of a short period will be described in detail.

As described above, in order to remove the displacement of synchronization of a short period, it is necessary to average the scanning lines of the print patterns of previous time to produce the imaginary scanning line.

In this case, the following averaging process is executed with respect to a timing axis.

$$D_{n(i,j)} = D_{n-1(i,j)} + (V_{n(i,j)} - D_{n-1(i,j)}) \times \frac{1}{2}$$

where $D_{n(i,j)}$ Averaged signal produced as a result that the image information of the print pattern during inspection is calculated averaging process.

$D_{n-1(i,j)}$: Averaged signal produced as a result that the image information of the printed pattern of previous time is calculated averaging process.

$V_{n(i,j)}$: Image information remained as the print pattern is detected during inspection.

i,j: Memory address

Figure 17:
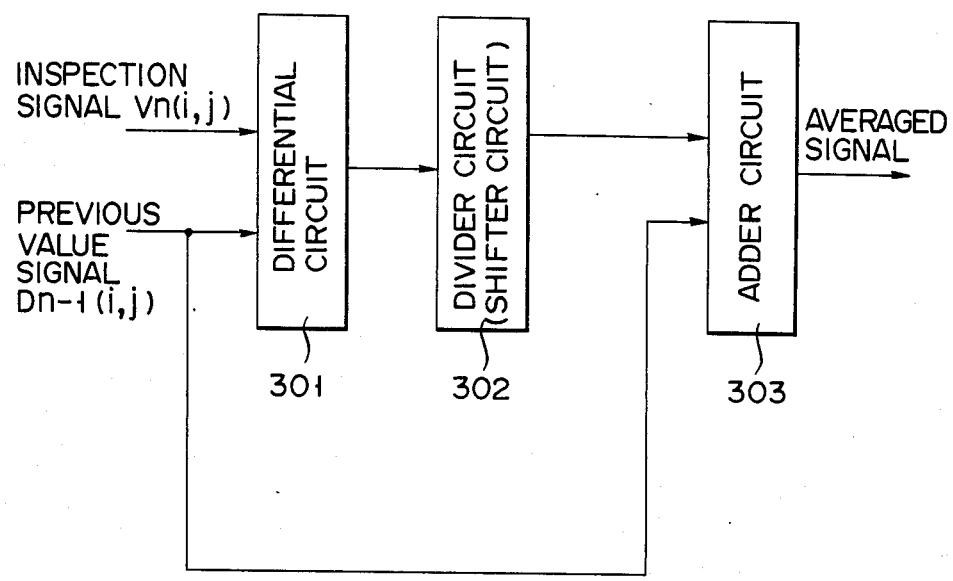
FIG. 17 is a block diagram of an averaging circuit in the embodiment of the invention.

As shown in FIG. 7, the previous value memory 16 stores the $D_{n-1(i,j)}$. As shown in FIG. 17, an averaging circuit 300 inputs the image information $V_{n(i,j)}$ and the previous value signal $D_{n-1(i,j)}$ of the memory 16, and calculates by a differential circuit 301 a differential signal $(V_{n(i,j)} - D_{n-1(i,j)})$. The differential circuit 301 is connected to a divider circuit 302 to produce the average value of the differential signal $(V_{n(i,j)} - D_{n-1(i,j)})$. When the constant to be divided in the divider 302 is integers of 2 or larger, the output is not mere average, but the differential circuit can calculate weighing average. The divider 302 is connected to an adder circuit 303, which adds the signal $D_{n-1(i,j)}$ and the average value transferred from the divider 302 and calculates the averaged signal $D_{n(i,j)}$.

The averaged signal $D_{n(i,j)}$ produced as described above is compared as the information to be inspected with the reference signal to average the detected image information at a timing axis, which means the same result as the inspection with respect to the imaginary scanning line of the print pattern of the printed sheet.

The averaged signal $D_{n(i,j)}$ is stored in the memory 16, and utilized for the averaging with the detected image information $V_{n+1(i,j)}$ of the next print pattern of the printed sheet.

As a result, the displacement of synchronization of a long period is removed as shown in FIG. 20, and the displacement of synchronization of a short period is also removed as shown in FIG. 21.

Figure 8:
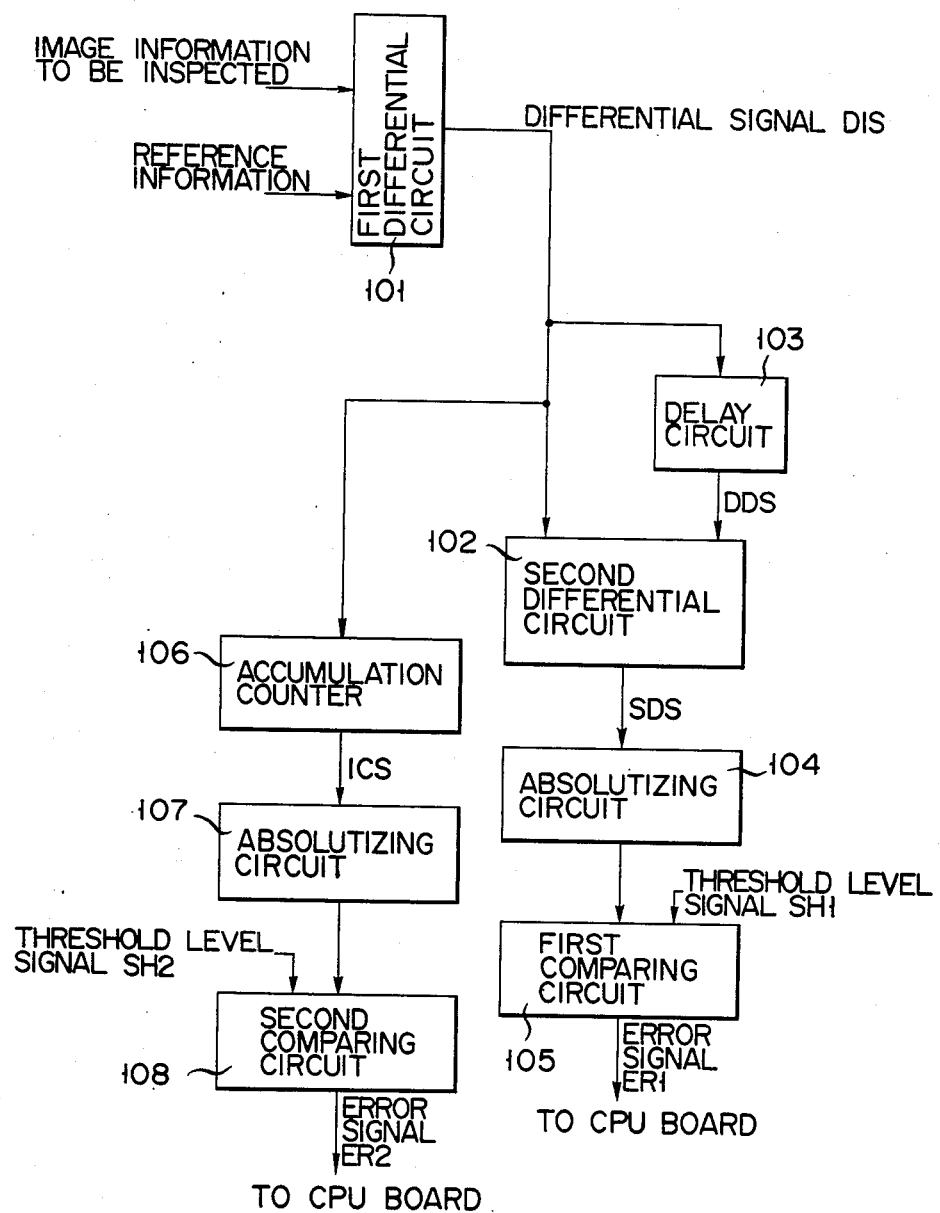
FIG. 8 is a block diagram of an error judging circuit in the embodiment of the invention.

More particularly, in FIG. 8, the information to be inspected and inputted to the first differential circuit 101 may use the image information inputted from the CCD line sensor camera 8 in the state that no displacement of synchronization occurs (e.g., in a sheet-fed press) as it is, but when the averaged signal $D_{n(i,j)}$ produced by utilizing the timing control circuit 200, the averaging circuit 300 and the previous value memory 16 in the state the displacement of synchronization occurs (e.g., in a web rotary press) is used, the error-judging circuit 100 can inspect in the state equivalent to the state no displacement of synchronization occurs to accurately inspect the print pattern of the printed sheet.

What is claimed is:

1. An inspecting device for a print for inspecting a printing defect occurred on a print pattern of a printed sheet comprising:

an optical detecting device for detecting image information at every pixel by optically scanning the print pattern of the printed sheet in a direction perpendicularly to the feeding direction of the printed sheet, reference information storing means for storing the image information at every pixel of the print pattern of the normal printed sheet as reference information, first differential calculating means for calculating the difference between the detected image information and the reference information;

delay means for delaying the differential signal produced by said first differential means by several pixels in the scanning direction of said optical detecting device;

second differential calculating means for calculating the difference between the differential signal produced by said first differential calculating means and the differential signal delayed and produced by said delay means; and comparing means for comparing the differential signal produced by said second differential calculating means with a predetermined allowable value to output an error signal for meaning the production of a printing defect on the print pattern when the differential signal exceeds the allowable range.

2. An inspecting device for a print according to claim 1, further comprising:

accumulating means for accumulating the differential signal produced by said first differential calculating means, and comparing means for comparing the accumulation signal produced by said accumulating means with a predetermined allowable value to output an error signal for production of the entire variation in color density on the print pattern when the accumulation signal exceeds the allowable range.

3. An inspecting device for a print according to claim 1, wherein said optical detecting device is a line sensor camera.

4. An inspecting device for a print according to claim 3, wherein said line sensor camera is a CCD line sensor.

5. An inspecting device for a print according to claim 3, wherein said line sensor camera is a MOS line sensor.

6. An inspecting device for a print according to claim 3, wherein said line sensor camera is a close contact line sensor.

7. An inspecting device for a print according to claim 1, wherein an optical filter having a transmission factor larger in the spectral transmission factor in a wavelength band of 400 nm to 500 nm than that in other visible light wavelength band of 500 nm to 700 nm is disposed between said optical detecting device and the printed sheet.

8. An inspecting device for a print according to claim 1, further comprising:

timing control means for correcting the scan starting timing of the print pattern of next set by calculating the averaged value of the displacements of synchronization per one print pattern of the printed sheets with a plurality of print patterns as a set and feeding back the value, and averaging means for averaging the image information of continuous two or more sheets produced by scanning at the corrected timing, thereby inputting the averaged information as the information to be inspected to said first differential calculating means.

* * * * *